US00PP14632P29

(12) United States Plant Patent
Warmerdam

(10) Patent No.: US PP14,632 P2
(45) Date of Patent: Mar. 23, 2004

(54) HOSTA PLANT NAMED 'EL NINO'

(50) Latin Name: *Hosta tardiflora*
Varietal Denomination: El Niño

(76) Inventor: Petrus Th. Warmerdam, Kapelleboslaan 16, 2204 AK Noordwijk (NL)

( * ) Notice: Subject to any disclaimer, the term of this patent is extended or adjusted under 35 U.S.C. 154(b) by 0 days.

(21) Appl. No.: 10/313,121

(22) Filed: Dec. 6, 2002

(51) Int. Cl.[7] ..... A01H 5/00
(52) U.S. Cl. ..... Plt./353
(58) Field of Search ..... Plt./353

*Primary Examiner*—Kent Bell
*Assistant Examiner*—Louanne Krawczewicz Myers
(74) *Attorney, Agent, or Firm*—C. A. Whealy

(57) ABSTRACT

A distinct cultivar of Hosta plant named 'El Nino', characterized by its relatively compact plant habit; bluish green and white variegated leaves; freely flowering habit; and violet blue-colored flowers that are positioned above the foliage on erect scapes.

2 Drawing Sheets

Botanical classification/cultivar designation: *Hosta tardiflora* cultivar El Niño.

BACKGROUND OF THE INVENTION

The present Invention relates to a new and distinct cultivar of Hosta plant, botanically known as *Hosta tardiflora*, and hereinafter referred to by the cultivar name El Niño.

The new Hosta originated from a cross-pollination in 1996 of the *Hosta tardiflora* cultivar Halcyon, not patented, as the female, or seed, parent with an unidentified selection of *Hosta tardiflora*, not patented, as the male, or pollen, parent. The cultivar El Niño was discovered and selected by the Inventor as a single plant within the progeny of the stated cross-pollination in a controlled environment in Noordwijk, The Netherlands.

Asexual reproduction of the new cultivar since March, 1999, by divisions harvested in Noordwijk, The Netherlands, has shown that the unique features of this new Hosta are stable and reproduced true to type in successive generations.

SUMMARY OF THE INVENTION

Plants of the cultivar El Niño have not been observed under all possible environmental conditions. The phenotype may vary somewhat with variations in environment such as temperature and light intensity without, however, any variance in genotype.

The following traits have been repeatedly observed and are determined to be the unique characteristics of 'El Niño'. These characteristics in combination distinguish 'El Niño' as a new and distinct cultivar:

1. Relatively compact plant habit.
2. Bluish green and white variegated leaves.
3. Freely flowering habit.
4. Violet blue-colored flowers that are positioned above the foliage on erect scapes.

Plants of the new Hosta can be compared to plants of the female parent, the cultivar Halcyon. Plants of the new Hosta differ primarily from plants of the cultivar Halcyon in leaf coloration as plants of the cultivar Halcyon have solid bluish green-colored leaves.

BRIEF DESCRIPTION OF THE PHOTOGRAPHS

The accompanying colored photographs illustrate the overall appearance of the new Hosta, showing the colors as true as it is reasonably possible to obtain in colored reproductions of this type. Colors in the photographs may differ slightly from the color values cited in the detailed botanical description which accurately describe the actual colors of the new Hosta.

The photograph on the first sheet comprises a side perspective view of a typical flowering plant of 'El Niño'.

The photograph at the top of the second sheet is a close-up view of typical leaves of 'El Niño'.

The photograph at the bottom of the second sheet is a close-up view of typical flowers of 'El Niño'.

DETAILED BOTANICAL DESCRIPTION

In the following description, color references are made to The Royal Horticultural Society Colour Chart, 1995 Edition, except where general terms of ordinary dictionary significance are used. Plants used for the aforementioned photographs and following description were about five years old and grown in an outdoor nursery and under conditions which closely approximate commercial production conditions during the summer in Noordwijk, The Netherlands.

Botanical classification: *Hosta tardiflora* cultivar El Niño.
Parentage:
- *Female, or seed, parent.*—*Hosta tardiflora* cultivar Halcyon, not patented.
- *Male, or pollen, parent.*—Unidentified selection of *Hosta tardiflora*, not patented.

Propagation:
- *Type.*—By divisions.
- *Time to initiate roots.*—About three months.
- *Root description.*—Fleshy, thick.

Plant description:
- *Form.*—Perennial flowering plant; initially upright becoming outwardly arching as leaves develop; mounded inverted triangle. Moderate to freely clumping. Appropriate for two-liter containers.

*Crop time.*—After rooting, about two years are required to produce finished flowering plants in two-liter containers.

*Plant height.*—About 50 cm.

*Plant diameter.*—About 75 cm.

*Foliage description.*—Leaves basal, simple, generally symmetrical, and long-persisting. Length: About 13 to 17 cm. Width: About 7 to 12 cm. Shape: Cordate. Apex: Apiculate. Base: Cordate. Margin: Entire. Texture, upper and lower surfaces: Glabrous, smooth; leathery. Luster, upper and lower surfaces: Dull. Venation pattern: Pinnate. Petiole length: About 20 to 25 cm. Color: Young and fully expanded foliage, upper surface: Center, 133B overlain with 188A; towards margins, 155D. Young and fully expanded foliage, lower surface: Center, 188A; towards margins, 155D. Petiole: Center, 191A; towards margins, 191D.

Flower description:

*Appearance.*—Single campanulate flowers with fused perianth arranged on upright racemes. Flowering stems arise from leaf axils. Typically about twelve flowering stems per plant. Flowers not persistent.

*Quantity of flowers.*—About twelve flowers per raceme.

*Natural flowering season.*—Summer in the Netherlands; flowering recurrent during this period.

*Fragrance.*—Not fragrant.

*Flower diameter.*—About 6 to 7 cm.

*Flower height* (*depth*).—About 9 to 17 cm.

*Perianth.*—Arrangement: Three interior and three exterior tepals; fused. Tepal length: About 4.5 cm. Tepal width: About 1 cm. Tepal shape: Elongated. Tepal apex: Apiculate. Tepal margin: Entire. Tepal texture, upper and lower surfaces: Smooth, satiny; glabrous. Tepal color: When opening and fully opened, upper surface: Centers, 85A; towards margins, 91C. When opening and fully opened, lower surface: 91C to 91D.

*Floral bracts.*—Quantity per flower: One. Shape: Lanceolate. Apex: Acute. Margin: Entire. Color: 146C; towards the margins, 76A.

*Scape.*—Length: About 30 to 45 cm. Aspect: Mostly upright. Texture: Smooth; glabrous. Color: 189B.

*Reproductive organs.*—Stamens: Quantity per flower: About five. Stamen length: About 4 cm. Stamen color: 4D. Anther length: About 3 cm. Anther color: 103B. Pollen color: 13A. Pistils: Quantity per flower: One. Style length: About 5 cm. Style color: 4D. Stigma color: 6B. Ovary color: Close to 145A.

*Fruit/seed description.*—Fruit and seed development has not been observed.

Disease/pest resistance: Plants of the new Hosta have not been noted to be resistant to pathogens and pests common to Hosta.

Weather tolerance: Plants of the new Hosta have been observed to be tolerant to rain, wind and temperatures from 0 to 35° C.

It is claimed:

1. A new and distinct cultivar of Hosta plant named 'El Nino', as illustrated and described.

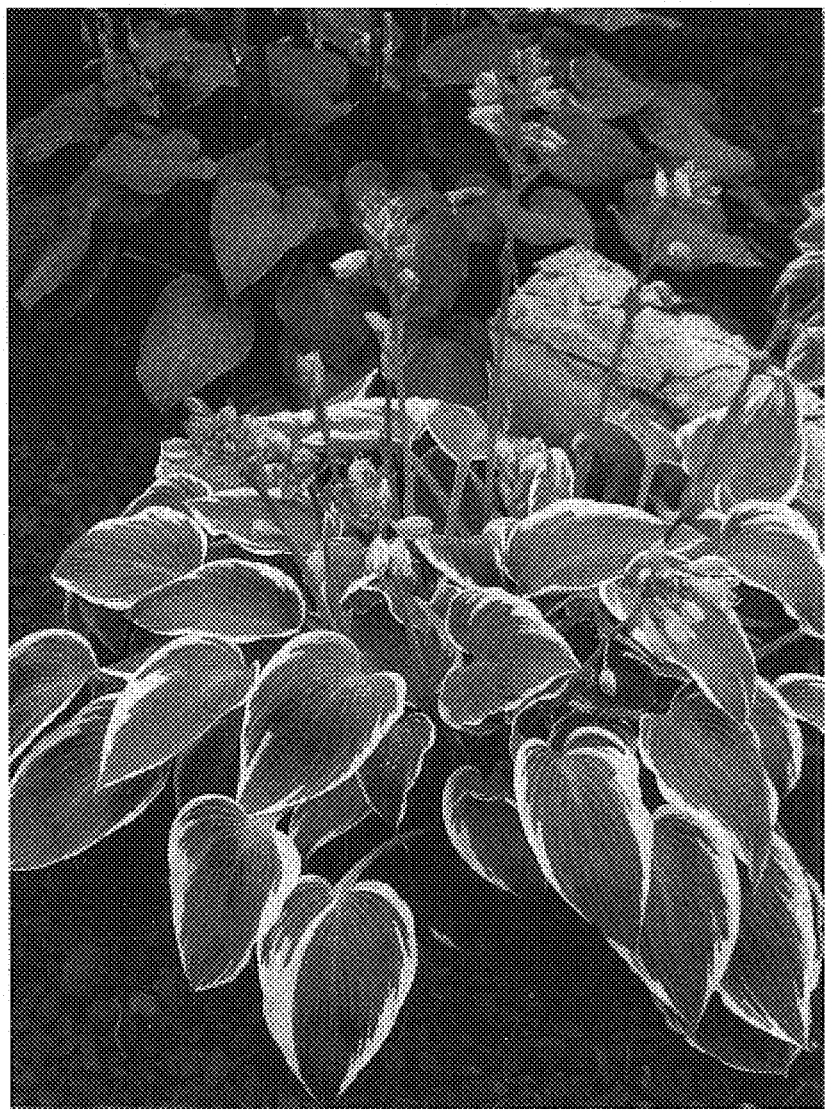

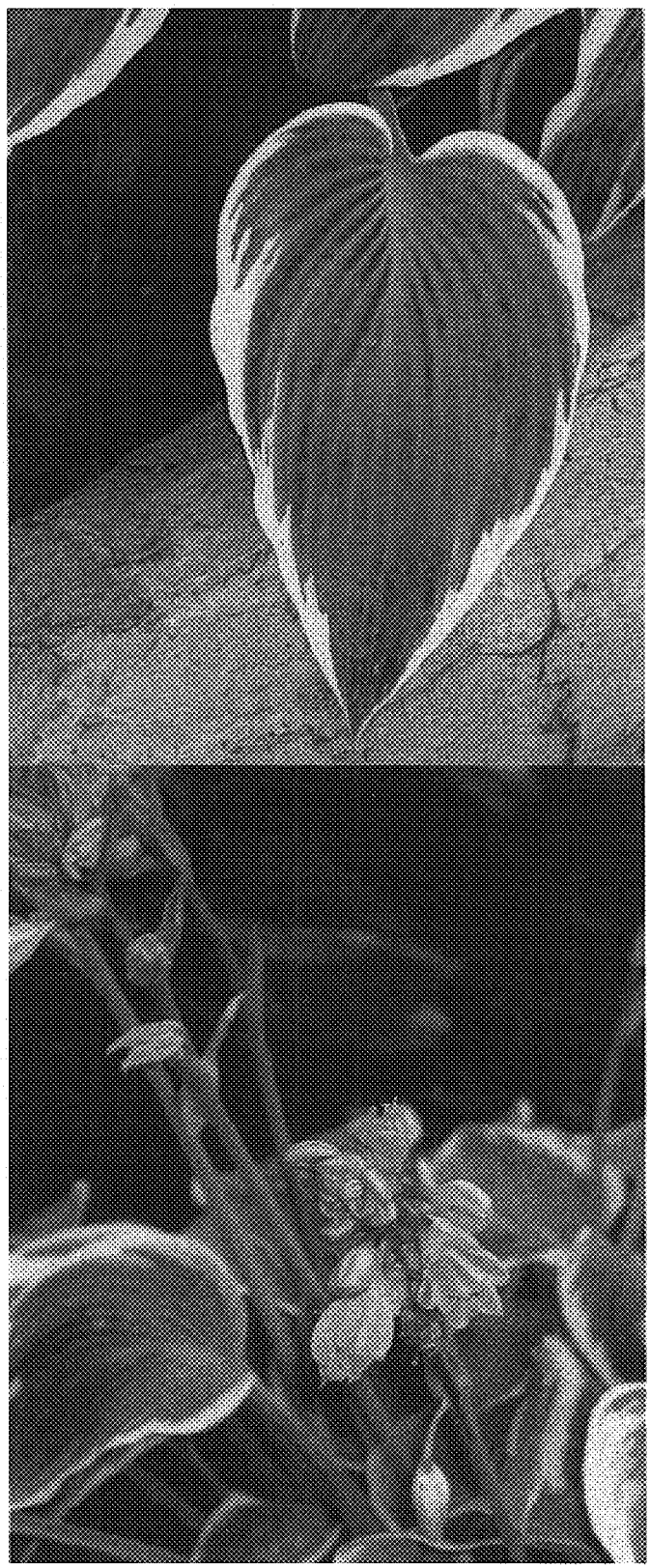

* * * * *